(12) United States Patent
Torii et al.

(10) Patent No.: US 6,888,012 B2
(45) Date of Patent: May 3, 2005

(54) PROCESS FOR PRODUCING OPTICALLY ACTIVE HALOHYDRIN COMPOUND

(75) Inventors: Takayoshi Torii, Kanagawa (JP); Takayuki Hamada, Kanagawa (JP); Tomoyuki Onishi, Kanagawa (JP); Kunisuke Izawa, Kanagawa (JP); Takao Ikariya, Tokyo (JP); Ryoji Noyori, Aichi (JP)

(73) Assignee: Ajinomoto Co., Inc., Tokyo (JP)

( * ) Notice: Subject to any disclaimer, the term of this patent is extended or adjusted under 35 U.S.C. 154(b) by 55 days.

(21) Appl. No.: 10/450,831

(22) PCT Filed: Dec. 18, 2001

(86) PCT No.: PCT/JP01/11105

§ 371 (c)(1),
(2), (4) Date: Jun. 25, 2003

(87) PCT Pub. No.: WO02/051781

PCT Pub. Date: Jul. 4, 2002

(65) Prior Publication Data

US 2004/0082820 A1 Apr. 29, 2004

(30) Foreign Application Priority Data

Dec. 25, 2000 (JP) .................................... 2000-391776
Aug. 3, 2001 (JP) .................................... 2001-237041
Oct. 12, 2001 (JP) .................................... 2001-314619

(51) Int. Cl.$^7$ .......................................... C07D 301/26
(52) U.S. Cl. ............................................. 549/522
(58) Field of Search ...................................... 549/522

(56) References Cited

U.S. PATENT DOCUMENTS 5,495,054 A    2/1996   Gao et al.
6,372,931 B1   4/2002   Blacker et al.
6,545,188 B2   4/2003   Blacker et al.

FOREIGN PATENT DOCUMENTS

| EP | 713848      | 5/1996  |
| EP | 736509      | 10/1996 |
| EP | 754669      | 1/1997  |
| JP | 11-335385   | 12/1999 |
| JP | 2000-169406 | 6/2000  |
| JP | 2000-212110 | 8/2000  |
| JP | 2000-256235 | 9/2000  |
| JP | 2000-327659 | 11/2000 |
| WO | 92/01804    | 2/1992  |
| WO | 97/20789    | 6/1997  |
| WO | 98/42643    | 10/1998 |
| WO | 01/17962    | 3/2001  |

OTHER PUBLICATIONS

Synlett, No. 10, pp. 1615–1617 1999.

Journal of Organic Chemistry, vol. 64, pp. 2186–2187 1999.

T. Thorpe et al.: "Efficient rodium and iridium–catalysed asymmetric transfer hydrogenation using water–soluble aminosulfonamide ligands" Tetrahedron Letters, vol. 42, pp. 4041–4043, 2001.

*Primary Examiner*—Taofiq Solola
(74) *Attorney, Agent, or Firm*—Oblon, Spivak, McClelland, Maier & Neustdat, P.C.

(57) ABSTRACT

A process of preparing an optically active halohydrin compound characterized by comprising asymmetric hydrogen transfer reduction of an α-haloketone compound in the presence of a group 9 transition metal compound having a substituted or unsubstituted cyclopentadienyl group and an optically active diamine compound. The asymmetric hydrogen transfer reduction is preferably conducted in the presence of a base.

16 Claims, No Drawings

PROCESS FOR PRODUCING OPTICALLY ACTIVE HALOHYDRIN COMPOUND

TECHNICAL FIELD

The present invention relates to a process for preparing an optically active halohydrin compound from an α-haloketone compound. The optically active halohydrin compound prepared according to the present invention is useful as, for example, an intermediate for pharmaceutical and agricultural chemicals.

BACKGROUND ART

Optically active halohydrin compounds, such as 2-chloro-1-phenylethanol, are known useful as intermediates for pharmaceutical or agricultural chemicals. Known techniques for producing these halohydrin compounds include a process comprising asymmetrically reducing an α-haloketone compound such as acetophenone by microbial cells (International Publication WO92/01804) and a process comprising asymmetrically reducing a similar α-haloketone compound through hydroboration using oxaborolidines as a catalyst (U.S. Pat. No. 5,495,054). The process involving use of microbial cells requires a large quantity of a solvent for dissolving the substrate, which cannot be necessarily seen as fit for industrial production. The process using oxaborolidines as a catalyst cannot be seen as favorable for industrial application from the aspect of safety because of toxicity of diborane used as a reducing agent. Accordingly, a process of preparing an optically active halohydrin compound which is efficient and suited to industrial application has been sought for.

Several processes are known for obtaining optically active benzyl alcohols through asymmetric reduction of acetophenones.

For example, International Publication WO97/20789 discloses that asymmetric reduction of acetophenone in the presence of a catalyst composed of an Ru complex and an optically active amine derivative gives an optically active 1-methylbenzyl alcohol. WO98/42643 and JP-A-11-335385 teach asymmetric reduction of acetophenone using an Rh complex in place of the Ru complex to prepare an optically active 1-methylbenzyl alcohol. *J. Org. Chem.*, 1999, 64, 2186–2187 reports a process of preparing optically active 1-methylbenzyl alcohol by asymmetric reduction of acetophenone in the presence of a catalyst comprising an Rh complex or an Ir complex and N-(p-toluenesulfonyl)-cyclohexanediamine.

These processes feature asymmetric hydrogen transfer reduction using transition metal complex catalysts. Substituting the acetophenones with the above-mentioned α-haloketone compounds such as 2-chloroacetophenone as a reaction substrate in any of these processes results in no reaction progress or extremely low yields as reported in *Synlett.*, 1999, 1615–1617. WO01/17962 discloses asymmetric hydrogen transfer reduction of 2-chloro-3'-nitroacetophenone by using a ruthenium catalyst. However, the process may not be necessarily regarded satisfactory for industrial production in view of optical yield and amount of catalyst.

It is an object of the present invention to provide a process of preparing an optically active halohydrin compound from an α-haloketone compound in high yield and high optical yield.

DISCLOSURE OF THE INVENTION

Under these technical circumstances, the present inventors have conducted extensive investigations and found, as a result, that transition metal complex-catalyzed asymmetric hydrogen transfer reduction of an α-haloketone compound efficiently proceeds in the presence of a specific compound of a group 9 transition metal and a specific diamine compound to establish an industrially excellent process of preparing an optically active α-halohydrin compound. The present invention has been completed based on this finding.

Completed based on the above finding, the present invention accomplishes the above object by providing a process of preparing an optically active halohydrin compound represented by general formula (3), characterized by comprising asymmetric hydrogen transfer reduction of an α-haloketone compound represented by general formula (1) in the presence of a group 9 transition metal compound having a substituted or unsubstituted cyclopentadienyl group and an optically active diamine compound represented by general formula (2).

(1)

wherein X represents a halogen atom; Y represents an aromatic hydrocarbon group, an aromatic heterocyclic group, an unsaturated hydrocarbon group or

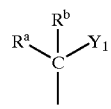

wherein $R^a$ and $R^b$ each represent a hydrogen atom, a substituted or unsubstituted alkyl group having 1 to 10 carbon atoms, a substituted or unsubstituted aryl group having 6 to 15 carbon atoms or a substituted or unsubstituted aralkyl group having 7 to 20 carbon atoms, in which the alkyl, aryl and aralkyl group may contain a hetero atom in the carbon skeleton thereof, and $Y_1$ represents an amino group, a protected amino group, a hydroxyl group or a protected hydroxyl group.

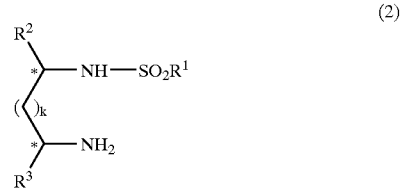
(2)

wherein $R^1$ represents an alkyl group, a fluoroalkyl group or a substituted or unsubstituted phenyl group; $R^2$ and $R^3$, which may be the same or different, each represent a substituted or unsubstituted phenyl group or a substituted or unsubstituted alkyl group having 1 to 10 carbon atoms, or $R^2$ and $R^3$ are taken together to form a ring; * indicates asymmetric carbon; k represents an integer of 0 to 3; and the steric configuration is (S,S) or (R,R).

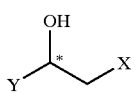
(3)

wherein X and Y are as defined above, and * indicates asymmetric carbon.

The present invention also provides a process of preparing an epoxide compound represented by general formula (4), characterized by comprising obtaining an optically active halohydrin compound according to the process described above and allowing a base to react on the compound.

(4)

wherein Y is as defined as for general formula (1); and * indicates asymmetric carbon.

BEST MODE FOR CARRYING OUT THE INVENTION

The present invention will be described with reference to its preferred embodiments.

In general formulae (1) and (3), Y represents an aromatic hydrocarbon group, an aromatic heterocyclic group, an unsaturated hydrocarbon group or a group represented by general formula (5). The aromatic hydrocarbon group includes one represented by general formula (6). The aromatic heterocyclic group includes one represented by general formula (7) and one represented by general formula (8).

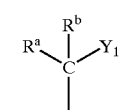
(5)

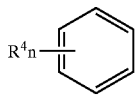
(6)

wherein $R^4$ represents a hydrogen atom or a substituent; n represents an integer of 1 to 5; and two or more substituents $R^4$ may be taken together to form a ring.

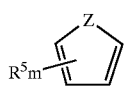
(7)

wherein $R^5$ represents a hydrogen atom or a substituent; m represents an integer of 1 to 3; Z represents O, S or NH; or two or more substituents $R^5$ may be taken together to form a ring.

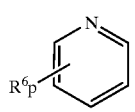
(8)

wherein $R^6$ represents a hydrogen atom or a substituent; p represents an integer of 1 to 3; or two or more substituents $R^6$ may be taken together to form a ring.

The α-haloketone compounds of general formula (1) which have the aromatic hydrocarbon group of general formula (6) or the aromatic heterocyclic group of general formula (7) or (8) are represented by general formulae (9) to (14) shown below.

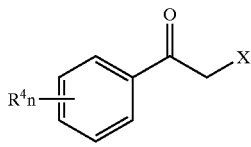
(9)

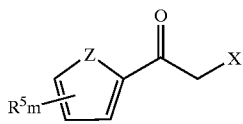
(10)

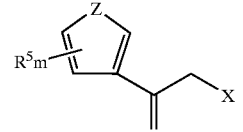
(11)

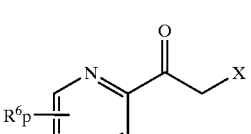
(12)

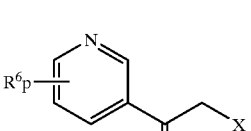
(13)

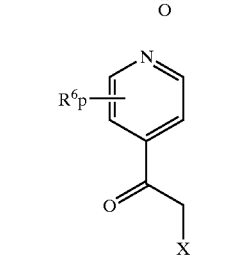
(14)

In general formula (9), where n is 2 or more, $R^4$'s may be the same or different, and two or more $R^4$'s may be connected to form a ring. In general formulae (10) and (11), where m is 2 or more, $R^5$'s may be the same or different, and two or more $R^5$'s may be connected to form a ring. In general formulae (12) to (14), where p is 2 or more, $R^6$'s may be the same or different, and two or more $R^6$'s may be connected to form a ring.

The α-haloketone compounds represented by general formula (1) wherein Y is an unsaturated hydrocarbon group include those represented by general formulae (15) and (16).

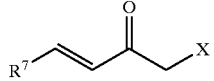
(15)

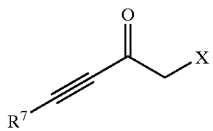

(16)

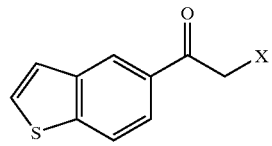

(19)

wherein R⁷ represents a hydrogen atom or a substituent

The substituents represented by R⁴, R⁵, R⁶, and R⁷ are arbitrary with no particular limitation. Examples thereof include alkyl groups, e.g., methyl, ethyl, n-propyl, isopropyl, n-butyl, isobutyl, sec-butyl, tert-butyl, and benzyl; cycloalkyl groups, e.g., cyclopropyl, cyclobutyl, cyclopentyl, and cyclohexyl; alkoxy groups, e.g., methoxy, ethoxy, n-propoxy, isopropoxy, n-butoxy, tert-butoxy, and benzyloxy; acyloxy groups, e.g., acetoxy and benzoyloxy; alkylthio groups, e.g., methylthio, ethylthio, n-propylthio, isopropylthio, n-butylthio, tert-butylthio, and benzylthio; acylthio groups, e.g., acetothio and benzoylthio; a hydroxyl group; halogen atoms, e.g., fluorine, chlorine, bromine, and iodine; carboxylic acid, sodium carboxylate; sulfonic acid, sodium sulfonate; a vinyl group; an allyl group; aryl groups, e.g., phenyl, naphthyl, furyl, thienyl, indolyl, and pyridyl; carbonyl groups, e.g., formyl, acetyl, trifluoroacetyl, benzoyl, methoxycarbonyl, ethoxycarbonyl, tert-butoxycarbonyl, vinyloxycarbonyl, allyloxycarbonyl, benzyloxycarbonyl, and methylaminocarbonyl; sulfonyl groups, such as alkylsulfonyl groups, arylsulfonyl groups, and sulfonamide groups; an amino group; primary amino groups, e.g., N-methylamino, N-ethylamino, N-n-propylamino, N-isopropylamino, N-n-butylamino, N-isobutylamino, N-tert-butylamino, N-benzylamino, N-methoxycarbonylamino, N-tert-butoxycarbonylamino, N-phenylamino, N-mesylamino, N-tosylamino, and formylamino; secondary amino groups, e.g., N,N-dimethylamino, N,N-diethylamino, N,N-benzylamino, N-ethyl-N-methylamino, N,N-di-n-propylamino, N,N-diisopropylamino, N,N-diphenylamino, N-methyl-N-phenylamino, N-methyl-N-benzylamino, N-mesyl-N-methylamino, piperidyl, and pyrrolidyl; tertiary amino groups, e.g., N,N,N-methylamino; a nitro group; a nitroso group; a cyano group; haloalkyl groups, e.g., monofluoromethyl, monochloromethyl difluoromethyl, dichloromethyl, trifluoromethyl, trichloromethyl, and pentafluoroethyl; and haloaryl groups, e.g., monofluorophenyl, trifluorophenyl, and pentafluorophenyl.

The α-haloketone compounds in which two or more of R⁴, R⁵, R⁶, and R⁷ form a ring include compounds represented by general formulae (17), (18), and (19).

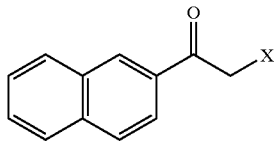

(17)

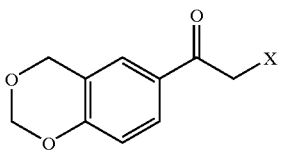

(18)

In general formulae (1) and (3) in which Y is a group of general formula (5), Rᵃ and Rᵇ each independently represent a hydrogen atom, a substituted or unsubstituted alkyl group having 1 to 10 carbon atoms, a substituted or unsubstituted aryl group having 6 to 15 carbon atoms or a substituted or unsubstituted aralkyl group having 7 to 20 carbon atoms or any of the recited groups which contains a hetero atom, e.g., nitrogen, oxygen, sulfur or phosphorus, in the carbon skeleton thereof The substituents of the recited groups are not particularly limited as long as they have no particular adverse influences on the asymmetric reduction of the present invention. Examples are alkoxy groups (preferably those containing 1 to 6 carbon atoms), a nitro group, alkyl groups (preferably those containing 1 to 6 carbon atoms), and halogen atoms. Where Rᵃ and Rᵇ are different, the compound represented by general formula (1) is optically active. In the present invention, however, it is not essential whether or not the compound of general formula (1) is optically active. It is extremely significant that the asymmetric reduction achieves high enantioselectivity in the resulting halohydrin compounds even when the compound of general formula (1) in which Y is a group of general formula (5) is optically inactive.

In general formula (5), Y¹ is an amino group, an amino group having one or two protective groups, a hydroxyl group or a hydroxyl group having a protective group. That is, Y¹ is represented by NP¹P² or OP³, wherein P¹ and P² each represent a hydrogen atom or an amino protective group, or they are taken together to represent a phthaloyl group; and P³ represents a hydroxyl protective group. P¹ and P² include the protective groups described in *Protective Groups in Organic Synthesis*, 3rd Ed., John Wiley & Sons, pp. 494–653. P¹ is preferably an acetyl group, a benzoyl group, an alkoxycarbonyl group, e.g., benzyloxycarbonyl or tert-butoxycarbonyl, a mesyl group, a tosyl group or a sulfonyl group, e.g., 2-nitrobenzenesulfonyl, 4-nitrobenzenesulfonyl or 2,4-dinitrobenzenesulfonyl. P² is preferably a hydrogen atom. P³ includes the hydroxyl protective groups shown in *Protective Groups in Organic Synthesis*, 3rd Ed., John Wiley & Sons, pp. 17–245.

In general formulae (1) and (3), X is a halogen atom as previously described. In the preparation process of the present invention it is particularly suitable for X to be chlorine.

Specific examples of the α-haloketone compound represented by general formula (1) are 2-chloroacetophenone, 2-chloro-3'-methylacetophenone, 2-chloro-3'-methoxyacetophenone, 2-chloro-3',4'-methylenedioxyacetophenone, 2-chloro-4'-phenylaccetophenone, 2-(chloroacetyl)furan, 2-chloro-3',4'-methylenedioxyacetophenone, 2-chloro-3'-hydroxyacetophenone, 2-chloro-2'-methoxyacetophenone, 2-chloro-4'-methoxyacetophenone, trans-4-benzo[1,3]dioxo-5-yl-1-chloro-3-buten-2-one, 2-chloro-3'-(dimethylamino)acetophenone, 2-chloro-3'-chloroacetophenone, 2-chloro-4'-chloroacetophenone, 2-chloro-3'-trifluoromethylacetophenone, 2-chloro4'-N-mesylaminoacetophenone, (3S)-3-tert-butoxycarbonylamino-1-chloro-4-phenyl-2-butanone, (3S)-

3-benzyloxycarbonylamino-1-chloro-4-phenyl-2-butanone, (3S)-3-(p-toluenesulfonyl)amino-1-chloro-4-phenyl-2-butanone, (3S)-3-benzyloxycarbonylamino-1-chloro-5-methyl-2-hexanone, (3S)-3-benzoylamino-1-chloro-4-phenyl-2-butanone, (3S)-3-benzyloxycarbonylamino-1-chloro-4-naphthyl-2-butanone, (3S)-3-benzyloxycarbonylamino-1-chloro-4-(p-fluorophenyl)-2-butanone, and (3S)-3-tert-butoxycarbonylamino-1-chloro-5-methyl-2-hexanone.

The asymmetric reduction of the α-haloketone compound according to the present invention is carried out in the presence of a group 9 transition metal compound having a substituted or unsubstituted cyclopentadienyl group and an optically active diamine compound represented by general formula (2), which constitute a catalyst system for asymmetric reduction.

The substituent of the substituted cyclopentadienyl group includes $C_1$ to $C_3$ alkyl groups. Preferred examples of the substituted or unsubstituted cyclopentadienyl group include a cyclopentadienyl group and a pentamethylcyclopentadienyl group, with a pentamethylcyclopentadienyl group being particularly preferred.

The group 9 transition metal includes rhodium, iridium and cobalt. Rhodium and iridium are preferred. Rhodium is particularly preferred.

Examples of the group 9 transition metal compound having a substituted or unsubstituted cyclopentadienyl group are di-μ-chlorodichlorobis(pentamethylcyclopentadienyl)dirhodium (III), di-μ-chlorodichlorobis(pentamethylcyclopentadienyl)diiridium (III). Di-μ-chlorodichlorobis(pentamethylcyclopentadienyl)dirhodium (III) is particularly preferred.

In the optically active diamine compound represented by general formula (2), $R^1$ includes a $C_1$ to $C_5$ alkyl group, a $C_1$ to $C_5$ fluoroalkyl group or a substituted or unsubstituted phenyl group. The substituent of the substituted phenyl group includes a $C_1$ to $C_5$ alkyl group, a $C_1$ to $C_5$ alkoxy group, and a halogen atom. The substituted or unsubstituted phenyl group is preferably a p-methylphenyl group.

In general formula (2), $R^2$ and $R^3$ include a phenyl group, a substituted phenyl group, an alkyl group having 1 to 10 carbon atoms, and a substituted alkyl group having 1 to 10 carbon atoms (preferably an alkyl group having 3 to 10 carbon atoms). $R^2$ and $R^3$ may be connected together to form a ring. $R^2$ and $R^3$ are preferably identical but may be different. The substituents include, but are not limited to, a $C_1$ to $C_5$ alkyl group, a $C_1$ to $C_5$ alkoxy group, a halogen atom, a cyano group, and a nitro group. Preferred examples of the alkyl group having 1 to 10 carbon atoms are isopropyl, isobutyl, tert-butyl, cyclopropyl, cyclobutyl, cyclopentyl, cyclohexyl, and 3,5-dimethylcyclohexyl. Preferred examples of the ring formed by $R^2$ and $R^3$ connected together are cyclopentyl, cyclohexyl, and cycloheptyl. $R^2$ and $R^3$ each preferably represent a phenyl group or a substituted phenyl group. Preferred examples of the substituted phenyl group are p-methylphenyl, 3,5-dimethylphenyl, p-nitrophenyl, and p-methoxyphenyl. It is particularly preferred that both $R^2$ and $R^3$ be a phenyl group.

The optically active diamine compound preferably has enantiometric and/or diastereometric purity to achieve increased yield and optical yield.

Of the optically active diamine compounds represented by general formula (2) in which k=0, preferred are those represented by general formula (20). Still preferred of them are (1R,2R)-N-(p-toluenesulfonyl)-1,2-diphenylethylenediamine and (1S,2S)-N-(p-toluenesulfonyl)-1,2-diphenylethylenediamine represented by formulae (21) and (22), respectively.

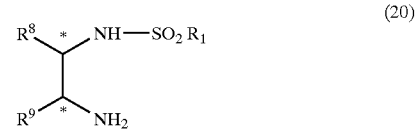

wherein $R^1$ is as defined above; $R^8$ and $R^9$, which may be the same or different, each represent a substituted or unsubstituted phenyl group; * indicates asymmetric carbon; and the steric configuration is (1S,2S) or (1R,2R).

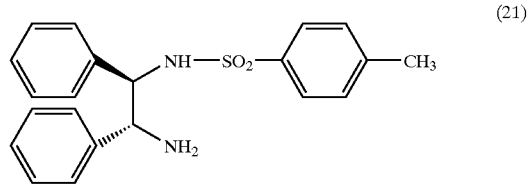

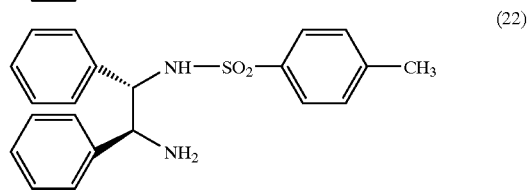

The diamine compounds represented by general formula (2) can be synthesized by processes known in the art, for example, the processes described in *J. Org. Chem.*, 1999, vol. 64, pp. 2186–2187, *Tetrahedron: Asymmetry*, 1999, vol. 10, pp. 991–1000, and *Tetrahedron: Asymmetry*, 1995, vol. 6, pp. 3–6.

As will be demonstrated by Examples given later, a halohydrin compound obtained by using an optically active diamine compound of general formula (2) having a (1R,2R)-configuration and a halohydrin compound obtained by using one having a (1S,2S)-configuration have opposite steric configurations. This is of importance for controlling the steric configuration of the halohydrin compound resulting from asymmetric reduction. For example, asymmetric reduction of 2-chloroacetophenone using a (1R,2R)-compound produces (S)-(+)-2-chloro-1-phenylethanol with high enantioselectivity. Use of a (1S,2S)-compound, on the other hand, results in production of (R)-(−)-2-chloro-1-phenylethanol with high enantioselectivity. Asymmetric reduction of (3S)-3-tert-butoxycarbonylamino-1-chloro-4-phenyl-2-butanone using a (1R,2R)-compound predominantly produces (2R,3S)-3-tert-butoxycarbonylamino-1-chloro-2-hydroxy-4-phenylbutane, and use of a (1S,2S)-compound results in production of (2S,3S)-3-tert-butoxycarbonylamino-1-chloro-2-hydroxy-4-phenylbutane as a main product.

In carrying out the process of the present invention, the group 9 transition metal compound having a substituted or unsubstituted cyclopentadienyl group and the optically active diamine compound of general formula (2) may be allowed to react in a solvent, and the resulting reaction mixture, to which a base is added, is used as such to serve for asymmetric reduction. The base may have been present during the reaction. The solvent is not particularly limited as far as is capable of dissolving the group 9 transition metal compound and the optically active diamine compound.

Preferred solvents include alcohols, such as methanol, ethanol, n-propyl alcohol, isopropyl alcohol, and butanol. From the viewpoint of reaction yield and economy, the reactants mixing ratio is preferably such that the amount of the optically active diamine compound is 0.5 to 20 equivalents, particularly 1 to 4 equivalents, to the transition metal of the transition metal compound. From the same viewpoint, the transition metal compound is preferably used in such amounts that the molar ratio of the transition metal of the transition metal compound to the α-haloketone compound of general formula (1) as a reaction substrate is 1/100 to 1/100000, particularly 1/10000 to 1/10000.

The process of the present invention is preferably carried out in the presence of a base. The existence of a base assures smooth progress of the asymmetric reduction reaction to provide the optically active halohydrin compound of general formula (3) in high optical yield.

The base to be used preferably has a $pK_b$ value of 8 or more, particularly 10 or more, at 25° C., for smooth progress of the asymmetric reduction. Useful bases include those represented by MY, wherein M represents an alkali metal or an alkaline earth metal; and Y represents a hydroxyl group, an alkoxy group, a mercapto group or a naphthyl group. Quaternary ammonium salts and amines are also useful as the base.

Examples of the bases are $KOH$, $KOCH_3$, $KOCH_2CH_3$, $KOCH(CH_3)_2$, $KOC(CH_3)_3$, $KC_{10}H_8$, $LiOH$, $LiOCH_3$, $LiOCH(CH_3)_2$, $LiOC(CH_3)_3$, $NaOH$, $NaOCH_3$, $NaOCH_2CH_3$, $NaOCH(CH_3)_2$, $NaC_{10}H_8$, $NaOC(CH_3)_3$, $K_2CO_3$, $KHCO_3$, $Na_2CO_3$, $NaHCO_3$, $Cs_2CO_3$, tetramethylammonium hydroxide, tetrabutylammonium hydroxide, trimethylamine, triethylamine, triisopropylamine, dimethylamine, diethylamine, diisopropylamine, methylamine, ethylamine, isopropylamine, and benzylamine. Particularly preferred of these bases are $KOH$, $KOCH(CH_3)_2$, $KOC(CH_3)_3$, and triethylamine. Where formic acid, a metal salt or ammonium salt of formic acid or an azeotropic mixture of formic acid and an amine is used as a hydrogen-donating organic compound as described infra, a preferred base is an amine, particularly triethylamine.

The base is preferably used in amounts of 0.5 to 50 equivalents, particularly 2 to 5 equivalents, to the transition metal compound. Where formic acid is used as a hydrogen-donating organic compound (hereinafter described), the base is preferably used in amounts of 0.01 to 5 equivalents, particularly 1 to 2 equivalents, to the α-haloketone compound of general formula (1).

In carrying out the process of the present invention, the chiral metal complex may be isolated for use as an asymmetric catalyst. More concretely, a group 9 transition metal compound having a substituted or unsubstituted cyclopentadienyl group is allowed to react with an equimolar amount of an optically active diamine compound represented by general formula (2) and double the molar amount of a base in a solvent at a temperature of from room temperature to about 80° C. usually for a period of 1 to 10 hours. The reaction mixture is cooled to about 20 to 0° C., and the resulting solid is collected by filtration to obtain a desired chiral metal complex. The base used includes the above-enumerated ones. The solvent is not particularly limited as far as is capable of dissolving the group 9 transition metal compound and the optically active diamine compound. Preferred solvents include the above-enumerated alcohols. A process of preparing such an chiral metal complex is described in *Organic Letters*, 1999, 1(6), 841–843, additional pages of Supporting Information (see URL http://www.pubs.acs.org/cgi-bin/suppinfo.pl?1990098q). Chiral metal complexes thus obtained are represented by general formula (23).

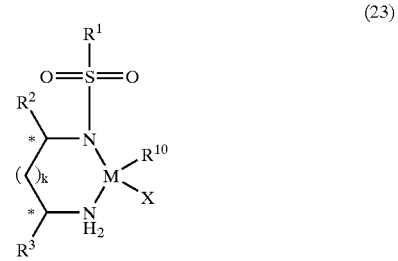

(23)

wherein $R^1$, $R^2$, $R^3$, k, and X are as defined above; $R^{10}$ represents a substituted or unsubstituted cyclopentadienyl group; M represents a group 9 transition metal; * indicates asymmetric carbon; and the steric configuration of the optically active amine compound moiety is (R,R) or (S,S).

Of the chiral metal complexes wherein k=0, still preferred ones are represented by general formula (24).

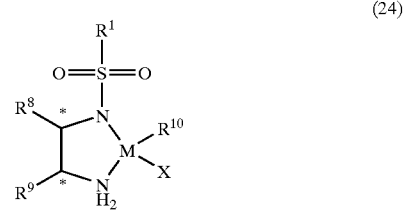

(24)

wherein $R^1$, $R^8$, $R^9$, $R^{10}$, M, and X are as defined above; * indicates asymmetric carbon; and the steric configuration of the optically active diphenylethylenediamine compound moiety is (1R,2R) or (1S,2S).

The chiral metal complex which is particularly suited to the process of the present invention includes one represented by general formula (24) in which $R^1$ is a p-methylphenyl group; $R^8$ and R9 are each a phenyl group; $R^{10}$ is a pentamethylcyclopentadienyl group; M is rhodium; and X is a chlorine atom.

In the process of the present invention, the asymmetric reduction is conducted in the presence of a hydrogen-donating organic or inorganic compound. The hydrogen-donating organic or inorganic compound includes alcohols, such as methanol, ethanol, n-propanol, isopropyl alcohol, butanol, and benzyl alcohol; formic acid; formic acid metal salts, such as sodium formate; ammonium formate; an azeotropic mixture of formic acid and an amine; unsaturated hydrocarbons or heterocyclic compounds having a saturated carbon bond in parts, such as tetralin and decalin; hydroquinone; and phosphorous acid. Preferred of them are hydrogen-donating organic compounds, such as alcohols, e.g., methanol, ethanol, n-propyl alcohol, isopropyl alcohol, butanol, and benzyl alcohol, formic acid, formic acid metal salts, e.g., sodium formate, ammonium formate, and an azeotropic mixture of formic acid and an amine. Among them, isopropyl alcohol, formic acid, and an azeotropic mixture of formic acid and an amine are suitable. Formic acid or an azeotropic mixture of formic acid and an amine is particularly suitable. Formic acid is the most suitable. These hydrogen-donating compounds can be used as a mixture of two or more thereof. The amount of the hydrogen-donating compound to be used in usually 1 equivalent or more, preferably 1 to 2 equivalents, to the α-haloketone compound represented by general formula (1). In using formic acid as a hydrogen-donating organic compound in the process of the invention, the above-described base is added. The amount of the base to be used is 0.01 to 5 equivalents, particularly 1 to 2 equivalents, to the α-haloketone compound of general formula (1) as previously described.

Where the hydrogen-donating organic or inorganic compound is liquid (e.g., formic acid or alcohols), it is capable of serving as a reaction solvent. In this case, the concentration of the α-haloketone compound of general formula (1), the reaction substrate, is usually in a range of from 0.01 to 20 mmol, preferably from 0.05 to 5 mol/l, while varying depending on the amount of the catalyst present.

In using formic acid or a metal or ammonium salt thereof, or a formic acid/amine azeotropic mixture as a hydrogen-donating organic compound, presence of a solvent is preferred. Useful solvents include isopropyl alcohol, methanol, butanol, acetonitrile, toluene, tetrahydrofuran, acetone, dimethylformamide, tert-butyl methyl ether, dichloromethane, ethyl acetate, ethylene glycol dimethyl ester, and water. These solvents may be used as a mixture of two or more thereof. Dichloromethane and ethyl acetate are particularly suitable solvents.

Where asymmetric reduction is performed in the presence of an alcohol, such as methanol, ethanol, n-propyl alcohol, isopropyl alcohol, butanol or benzyl alcohol, as a hydrogen-donating organic compound, it is necessary that the substituents represented by $R^4$ to $R^7$ in the groups or compounds represented by general formulae (6) through (16) be an electron-donating group (i.e., Y in general formulae (1), (3), and (4) should be an electron-donating aromatic group). Electron-donating groups include alkyl groups, e.g., methyl, ethyl, n-propyl, isopropyl, n-butyl, isobutyl, sec-butyl, tert-butyl, and benzyl; cycloalkyl groups, e.g., cyclopropyl, cyclobutyl, cyclopentyl, and cyclohexyl; alkoxy groups, e.g., methoxy, ethoxy, n-propoxy, isopropoxy, n-butoxy, tert-butoxy, and benzyloxy; acyloxy groups, e.g., acetoxy and benzoyloxy; alkylthio groups, e.g., methylthio, ethylthio, n-propylthio, isopropylthio, n-butylthio, tert-butylthio, and benzylthio; acylthio groups, e.g., acetothio and benzoylthio; dialkylamino groups, e.g., dimethylamino, diethylamino, di-n-propylamino, and dibenzylamino; a vinyl group, a phenyl group, a naphthyl group, a furyl group, a thienyl group, and an indolyl group.

The reaction system according to the process of the invention may be pressurized with hydrogen. The pressure is preferably 1 to 100 atm., still preferably 1 to 10 atm. Hydrogen pressurizing is unnecessary in some reaction systems.

The reaction temperature of the asymmetric reduction usually ranges from −20 to 100° C. A range of from 25 to 40° C. is preferred for yield and economy. The reaction time, while varying according to the other reaction conditions, usually ranges from several minutes to about 100 hours. A range of from 2 to 24 hours is preferred for yield and economy. The reaction can be ceased by addition of water and an acid, such as hydrochloric acid or citric acid.

The reaction product, i.e., the optically active halohydrin compound represented by general formula (3) can be isolated and purified through common purification operations, such as extraction, distillation, recrystallization, and chromatography. Specific examples of the thus obtained optically active halohydrin compounds are (S)-(+)-2-chloro-1-phenylethanol, (R)-(−)-2-chloro-1-phenylethanol, (+)-2-chloro-1-(3'-tolyl)ethanol, (+)-2-chloro-1-(3'-methoxyphenyl)ethanol, (+)-2-chloro-1-(3',4'-methylenedioxy)phenylethanol, (+)-2-chloro-1(4'-phenylphenyl)ethanol, (+)-2-chloro-1-(2'-furyl)ethanol, (+)-2-chloro-1-(3',4'-methylenediphenyl)ethanol, (+)-2-chloro-1-(3'-hydroxyphenyl)ethanol, (+)-2-chloro-1-(2'-methoxyphenyl)ethanol, (+)-2-chloro-1-(4'-methoxyphenyl)ethanol, trans-4-benzo[1,3]dioxo-5-yl-1-chloro-3-buten-2-ol, (+)-2-chloro-1-(3'-dimethylaminophenyl)ethanol, (+)-2-chloro-1-(3'-chlorophenyl)ethanol, (+)-2-chloro-1-(4'-chlorophenyl)ethanol, (+)-2-chloro-1-(3'-trifluoromethylphenyl)ethanol, (+)2-chloro-1(4'-N-mesylaminophenyl)ethanol, (2R,3S)-3-tert-butoxycarbonylamino-1-chloro-2-hydroxy-4-phenylbutane, (2S,3S)-3-tert-butoxycarbonylamino-1-chloro-2-hydroxy-4-phenylbutane, (2R,3S)-3-benzyloxycarbonylamino-1-chloro-2-hydroxy-4-phenylbutane, (2S,3S)-3-benzyloxycarbonylamino-1-chloro-2-hydroxy-4phenylbutane, (2R,3S)-3-(p-toluenesulfonyl)amino-1-chloro-2-hydroxy-4-phenylbutane, (2S,3S)-3-(p-toluenesulfonyl)amino-1-chloro-2-hydroxy-4-phenylbutane, (2R,3S)-3-benzyloxycarbonylamino-1-chloro-2-hydroxy-5-methylhexane, (2S,3S)-benzyloxycarbonylamino-1-chloro-2-hydroxy-5-methylhexane, (2R,3S)-3-benzoylamino-1-chloro-2-hydroxy-4-phenylbutane, (2S,3S)-3-benzoylamino-1-chloro-2-hydroxy-4-phenylbutane, (2R,3S)-3-benzyloxycarbonylamino-1-chloro-2-hydroxy-4-naphthylbutane, (2S,3S)-3-benzyloxycarbonylamino-1-chloro-2-hydroxy-4-naphthylbutane, (2R,3S)-3-benzyloxycarbonylamino-1-chloro-2-hydroxy-4-fluorophenyl)butane, (2S,3S)-3-benzyloxycarbonylamino-1-chloro-2-hydroxy-4-(p-fluorophenyl)butane, (2R,3S)-3-tert-butoxycarbonylamino-1-chloro-2-hydroxy-5-methylhexane, and (2S,3S)-3-tert-butoxycarbonylamino-1-chloro-2-hydroxy-5-methylhexane.

Allowing a base to react on the optically active halohydrin compound thus obtained produces an optically active epoxide compound represented by general formula (4). The optically active epoxide compound can be led to pharmaceuticals, agricultural chemicals, dyes, and the like. The base to be used includes those recited above for use in the asymmetric reduction. In particular, inorganic bases, such as KOH, NaOH, and K2CO$_3$, are suitable. The optically active epoxy compound can easily be obtained by, for example, performing reaction in the presence of the base in an equimolar or more amount with respect to the substrate preferably at a temperature of from room temperature to about 100° C. usually for a period of 1 to 24 hours.

EXAMPLES

The present invention will now be illustrated in greater detail with reference to Examples, but it should be understood that they are not construed as limiting the present invention. In Examples, the optical purity was decided by optically active high-performance liquid chromatography.

Example 1

A solution of di-$\mu$-chlorodichlorobis (pentamethylcyclopentadienyl)dirhodium (III) (155 mg, 0.025 mmol) and (1R,2R)-N-(p-toluenesulfonyl)-1,2-diphenylethylenediamine (36.6 mg, 0.1 mmol) in isopropyl alcohol (25.0 ml) was heated at 80° C. for 20 minutes while stirring. After cooling the solution to room temperature, a 0.1 M potassium tert-butoxide isopropyl alcohol solution (2.5 ml, 0.25 mmol) and an isopropyl alcohol solution (22.5 ml) of 2-chloroacetophenone (773.0 mg, 5.0 mmol) as a reaction substrate were added thereto, followed by stirring at room temperature for 14 hours. After completion of the reaction, the solvent was removed by evaporation, and the residue was purified by silica gel column chromatography to give a desired compound, (+)-2-chloro-1-phenylethanol (732.9 mg; yield: 93.6%; optical purity: 97.5% ee).

Example 2

A solution of (+)-2-chloro-1-phenylethanol (156.6 mg, 1.0 mmol, 97.5% ee) in dichloromethane (2.0 ml) and a 2.0 M aqueous solution of sodium hydroxide (1.0 ml, 2.0 mmol) were mixed and stirred at room temperature for 4 hours. To the solution was added dichloromethane (2.0 ml), and the dichloromethane layer was washed with a saturated sodium chloride aqueous solution and dried over anhydrous sodium sulfate. The solvent was removed by evaporation. The residue was purified by silica gel column chromatography to give a desired compound, (+)-styrene oxide (115.2 mg; yield: 95.9%; optical purity: 97.5% ee).

Example 3

A solution of di-$\mu$-chlorodichlorobis(pentamethylcyclopentadienyl)dirhodium (III) (3.1 mg, 0.005 mmol) and (1R,2R)-N-(p-toluenesulfonyl)-1,2-diphenylethylenediamine (7.3 mg, 0.02 mmol) in isopropyl alcohol (5.0 ml) was heated at 80° C. for 20 minutes while stirring. After cooling the solution to room temperature, a 0.1 M potassium tert-butoxide isopropyl alcohol solution (0.5 ml, 0.05 mmol) and an isopropyl alcohol solution (4.5 ml) of 2-chloro-3'-methylacetophenone (168.6 mg, 1.0 mmol) as a reaction substrate were added thereto, followed by stirring at room temperature for 14 hours. After completion of the reaction, the solvent was removed by evaporation, and the residue was purified by silica gel column chromatography to give a desired compound, (+)-2-chloro-1-(3'-methylphenyl)ethanol (158.6 mg; yield: 93.0%; optical purity: 95.6% ee).

Example 4

A desired compound, (+)-2-chloro-1-(3'-methoxyphenyl)ethanol, was obtained in the same manner as in Example 3, except for replacing 2-chloro-3'-methylacetophenone as a reaction substrate with 2-chloro-3'-methoxyacetophenone (184.6 mg, 1 mmol). The yield was 93.7%, and the optical purity was 98.4% ee.

Example 5

A desired compound, (+)-2-chloro-1-(3',4'-methylenediphenyl)ethanol, was obtained in the same manner as in Example 3, except for replacing 2chloro-3'-methylacetophenone as a reaction substrate with 2-chloro-3',4'-methylenedioxyacetophenone (198.6 mg, 1 mmol). The yield was 96.3%, and the optical purity was 97.8% ee.

Example 6

A desired compound, (+)-2-chloro-1-(4'-phenylphenyl)ethanol, was obtained in the same manner as in Example 3, except for replacing 2-chloro-3'-methylacetophenone as a reaction substrate with 2-chloro-4'-phenylacetophenone (230.7 mg, 1 mmol). The yield was 95.7%, and the optical purity was 98.7% ee.

Example 7

A desired compound, (+)-2-chloro-1-(2'-furyl)ethanol, was obtained in the same manner as in Example 3, except for replacing 2-chloro-3'-methylacetophenone as a reaction substrate with 2-(chloroacetyl)furan (144.6 mg, 1 mmol). The yield was 94.4%, and the optical purity was 98.7% ee.

Example 8

A desired compound, (+)-2-chloro-1-(3'-hydroxyphenyl)ethanol, was obtained in the same manner as in Example 3, except for replacing 2-chloro-3'-methylacetophenone as a reaction substrate with 2-chloro-3'-hydroxyacetophenone (170.6 mg, 1 mmol). The yield was 94.8%, and the optical purity was 98.8% ee.

Example 9

A desired compound, (+)-2-chloro-1-(2'-methoxyphenyl)ethanol, was obtained in the same manner as in Example 3, except for replacing 2-chloro-3'-methylacetophenone as a reaction substrate with 2-chloro-2'-methoxyacetophenone (184.6 mg, 1 mmol). The yield was 95.9%, and the optical purity was 93.8% ee.

Example 10

A desired compound, (+)-2-chloro-1-(4'-methoxyphenyl)ethanol, was obtained in the same manner as in Example 3, except for replacing 2-chloro-3'-methylacetophenone as a reaction substrate with 2-chloro-4'-methoxyacetophenone (184.6 mg, 1 mmol). The yield was 95.9%, and the optical purity was 97.6% ee.

Example 11

A desired compound, trans-4-benzo[1,3]dioxo-5-yl-1-chloro-3-buten-2-ol, was obtained in the same manner as in Example 3, except for replacing 2-chloro-3'-methylacetophenone as a reaction substrate with trans-4benzo[1,3]dioxo-5-yl-1-chloro-3-buten-2-one (224.6 mg, 1 mmol). The yield was 96.8%, and the optical purity was 95.3% ee.

Example 12

A solution of di-$\mu$-chlorodichlorobis(pentamethylcyclopentadienyl)dirhodium (III) (1.5 mg, 0.0025 mmol) and (1R,2R)-N-(p-toluenesulfonyl)-1,2-diphenylethylenediamine (3.7 mg, 0.01 mmol) in isopropyl alcohol (4.75 ml) was heated at 80° C. for 20 minutes while stirring. After cooling the solution to room temperature, a 0.1 M potassium tert-butoxide isopropyl alcohol solution (0.25 ml, 0.025 mmol) and 2-chloro-3'-(dimethylamino)acetophenone (98.8 mg, 0.5 mmol) as a reaction substrate were added thereto, followed by stirring at room temperature for 14 hours. After completion of the reaction, the solvent was removed by evaporation, and the residue was purified by silica gel column chromatography to give a desired compound, (+)-2-chloro-1-(3'-dimethylaminophenyl)ethanol (95.3 mg; yield: 95.3%; optical purity: 98.8% ee).

Example 13

2-Chloro-3'-chloroacetophenone (945.0 mg, 5.0 mmol), triethylamine (0.73 ml, 5.25 mmol), and formic acid (0.23 ml, 5.25 mmol) were added to an ethyl acetate (5.0 ml) solution containing chloro(pentamethylcyclopentadienyl)rhodium (III) (1R,2R)-N-(p-toluenesulfonyl)-1,2-diphenylethylenediamine (1.35 mg, 0.002 mmol, s/c=5000) which was prepared in the same manner as described in *Organic Letters*, 1999, vol. 1, pp. 841–843, Supporting Information (see the above-described URL), and the mixture was stirred at room temperature for 2 hours. After completion of the reaction, 1 M hydrochloric acid (5.3 ml) was added, and the reaction product was extracted with ethyl acetate (5 ml) and dried over magnesium sulfate. Evaporation of the solvent yielded a desired compound, (+)-2-chloro-1-(3'-chlorophenyl)ethanol (891.5 mg; yield: 93.4%; optical purity: 93.8% ee).

Example 14

2-Chloro-4'-chloroacetophenone (189.6 mg, 1.0 mmol) and a formic acid/triethylamine azeotropic mixture (0.2 ml) were added to a solution of chloro(pentamethylcyclopentadienyl)rhodium (III) (1R,2R)-N-(p-toluenesulfonyl)-1,2-diphenylethylenediamine (0.67 mg, 0.001 mmol, s/c=1000) in ethyl acetate (2.0 ml), followed by stirring at room temperature for 2 hours. After completion of the reaction, 1 M hydrochloric acid (1.2 ml) was added, and the reaction product was extracted with ethyl acetate (2 ml) and dried over magnesium sulfate. Evaporation of the solvent gave a desired compound, (+)-2-chloro-1-(4'-chlorophenyl)ethanol (172.8 mg; yield: 90.2%; optical purity: 91.6% ee).

Example 15

A desired compound, (+)-2-chloro-1-(3'-methoxyphenyl)ethanol, was obtained in the same manner as in Example 14, except for replacing 2-chloro-4'-chloroacetophenone as a reaction substrate with 2-chloro-3'-methoxyacetophenone (184.6 mg, 1 mmol). The yield was 90.3%, and the optical purity was 95.8% ee.

Example 16

A desired compound, (+)-2-chloro-1-(4'-methoxyphenyl)ethanol, was obtained in the same manner as in Example 14, except for replacing 2-chloro-4'-chloroacetophenone as a reaction substrate with 2-chloro-4'-methoxyacetophenone (184.6 mg, 1 mmol). The yield was 90.3%, and the optical purity was 95.8% ee.

Example 17

A desired compound, (+)-2-chloro-1-(3'-hydroxyphenyl)ethanol, was obtained in the same manner as in Example 14, except for replacing 2-chloro-4'-chloroacetophenone as a reaction substrate with 2-chloro-3'-hydroxyacetophenone (170.6 mg, 1 mmol). The yield was 93.0%, and the optical purity was 94.8% ee.

Example 18

A desired compound, (+)-2-chloro-1-(3'-trifluoromethylphenyl)ethanol, was obtained in the same manner as in Example 14, except for replacing 2-chloro-4'-chloroacetophenone as a reaction substrate with 2-chloro-3'-trifluoromethylacetophenone (222.6 mg, 1 mmol). The yield was 80.8%, and the optical purity was 95.5% ee.

Example 19

A desired compound, (+)-2-chloro-1-(3'-methylphenyl)ethanol, was obtained in the same manner as in Example 14, except for replacing 2-chloro-4'-chloroacetophenone as a reaction substrate with 2-chloro-3'-methylacetophenone (150.6 mg, 1 mmol). The yield was 92.2%, and the optical purity was 96.4% ee.

Example 20

A desired compound, (+)-2-chloro-14'-N-mesylaminophenyl)ethanol, was obtained in the same manner as in Example 14, except for replacing 2-chloro-4'-chloroacetophenone as a reaction substrate with 2-chloro-4'-N-mesylaminoacetophenone (274.7 mg, 1 mmol). The yield was 80.4%, and the optical purity was 97.5% ee.

Example 21

A desired compound, (+)-2-chloro-1-(3',4'-methylenedioxyphenyl)ethanol, was obtained in the same manner as in Example 14, except for replacing 2-chloro-4'-chloroacetophenone as a reaction substrate with 2-chloro-3',4'-methylenedioxyacetophenone (198.6 mg, 1 mmol). The yield was 93.1%, and the optical purity was 95.2% ee.

Example 22

2-Chloro-2'-methoxyacetophenone (186.6 mg, 1.0 mmol) and a formic acid/triethylamine azeotropic mixture (0.2 ml) were added to a solution of chloro(pentamethylcyclopentadienyl)rhodium (III) (1R,2R)-N-(p-toluenesulfonyl)-1,2-diphenylethylenediamine (1.35 mg, 0.002mmol, s/c=500) in ethyl acetate (2.0ml), followed by stirring at room temperature for 2 hours. After completion of the reaction, 1 M hydrochloric acid (1.2 ml) was added, and the reaction product was extracted with ethyl acetate (2 ml) and dried over magnesium sulfate. Evaporation of the solvent gave a desired compound, (+)-2-chloro-1-(2'-methoxyphenyl)ethanol (170.6 mg; yield: 90.4%; optical purity: 95.2% ee).

Example 23

2-Chloroacetophenone (154.0 mg, 1.0 mmol) and a formic acid/triethylamine azeotropic mixture (0.2 ml) were added to a solution of chloro(pentamethylcyclopentadienyl)rhodium (III) (1R,2R)-N-(p-toluenesulfonyl)-1,2-diphenylethylenediamine (0.67 mg, 0.001 mmol, s/c=1000) in ethyl acetate (1.0 ml), followed by stirring at room temperature for 2 hours. After completion of the reaction, purification by silica gel column chromatography furnished a desired compound, (S)-(+)-2-chloro-1-phenylethanol (145.1 mg; yield: 93.0%; optical purity: 96.6% ee).

Example 24

In the same manner as in Example 23, except for using a solution of chloro(pentamethylcyclopentadienyl)rhodium (III) (1S,2S)-N-(p-toluenesulfonyl)-1,2-diphenylethylenediamine (0.67 mg, 0.001 mmol, s/c=1000) in ethyl acetate (1.0 ml), a desired compound, (R)-(−)-2-chloro-1-phenylethanol, was obtained (143.2 mg; yield: 91.7%; optical purity: 96.4% ee).

Example 25

(3S)-3-tert-Butoxycarbonylamino-1-chloro-4-phenyl-2-butanone (1.49 g, 5.0 mmol), 90% formic acid (0.224 ml, 5.25 mmol), and triethylamine (0.730 ml, 5.25 mmol) were added to a solution of chloro(pentamethylcyclopentadienyl)rhodium (III) (1R,2R)-N-(p-toluenesulfonyl-1,2-diphenylethylenediamine (3.4 mg, 0.005 mmol, s/c=1000) in ethyl acetate (7.0 ml), followed by stirring at room temperature for 2 hours. After completion of the reaction, the reaction mixture was quantitatively analyzed by HPLC to confirm production of a desired compound, (2R, 3S)-3-tert-butoxycarbonylamino-1-chloro-2-hydroxy-4phenylbutane (1.50 g; yield: 99.9%). The production ratio of the desired (2R,3S)-form to the isomeric (2S,3S)-form, (2R,3S):(2S,3S), was found to be 9.0:1.

Example 26

(3S)-3-tert-Butoxycarbonylamino-1-chloro-4-phenyl-2-butanone (1.49 g, 5.0 mmol), 90% formic acid (0.224 ml, 5.25 mmol), and triethylamine (0.730 ml, 5.25 mmol) were added to a solution of chloro(pentamethylcyclopentadienyl) rhodium (III) (1S,2S)-N-(p-toluenesulfonyl)-1,2-diphenylethylenediamine (3.4 mg, 0.005 mmol, s/c=1000) in dichloromethane (10.0 ml), followed by stirring at room temperature for 1 hour. Dichloromethane (20.0 ml) was added to the reaction mixture, and the stirring was continued for 1 hour at room temperature. After completion of the reaction, the reaction mixture was quantitatively analyzed by HPLC to confirm production of a desired compound, (2S, 3S)-3-tert-butoxycarbonylamino-1-chloro-2-hydroxy-4-phenylbutane (1.50 g; yield: 99.9%). The production ratio of the desired (2S,3S)-form to the isomeric (2R,3S)-form, (2S,3S):(2R,3S), was found to be 12.5:1. The resulting dichloromethane solution was evaporated, and the residue was crystallized from a mixed solvent of water, toluene and ethanol (1:1:3) to give a mixture at a (2S,3S) to (2R,3S) ratio of 99.6:0.4 in a yield of 80%.

Example 27

(3S)-3-Benzyloxycarbonylamino-1-chloro-4-phenyl-2-butanone (331.8 mg, 1.0 mmol) and a formic acid/triethylamine azeotropic mixture (0.2 ml) were added to a solution of chloro(pentamethylcyclopentadienyl)rhodium (III) (1R,2R)-N-(p-toluenesulfonyl)-1,2-diphenylethylenediamine (0.67 mg, 0.001 mmol, s/c=1000) in ethyl acetate (1.0 ml), followed by stirring at room temperature for 2 hours. After completion of the reaction, the reaction mixture was purified by silica gel column chromatography to give a desired compound, (2R, 3S)-3-benzyloxycarbonylamino-1-chloro-2-hydroxy-4-phenylbutane (320.1 mg; yield: 95.8%). HPLC analysis revealed that the production ratio of the desired (2R,3S)-form to the isomeric (2S,3S)-form, (2R,3S):(2S,3S), was 8.5:1. The results of elementary analysis were as follows.

Calcd. C, 64.77%; H, 6.04%; N, 4.20%. Found C, 64.93%; H, 5.97%; N, 4.08%.

Example 28

In the same manner as in Example 27, except for using a solution of chloro(pentamethylcyclopentadienyl)rhodium (III) (1S,2S)-N-(p-toluenesulfonyl)-1,2-diphenylethylenediamine (0.67 mg, 0.001 mmol, s/c=1000) in ethyl acetate (1.0 ml), a desired compound (2S,3S)-3-benzyloxycarbonylamino-1-chloro-2-hydroxy4-phenylbutane (322.4 mg; yield: 96.5%) was obtained. HPLC analysis revealed that the production ratio of the desired (2S,3S)-form to the isomeric (2R,3S)-form, (2S,3S):(2R, 3S), was 10.2:1. The results of elementary analysis were as follows.

Calcd. C, 64.77%; H, 6.04%; N, 4.20%. Found C, 64.85%; H, 5.86%; N, 4.02%.

Example 29

(3S)-3-(p-Toluenesulfonyl)amino-1-chloro-4-phenyl-2-butanone (175.9 mg, 0.5 mmol) and a formic acid/triethylamine azeotropic mixture (0.1 ml) were added to a solution of chloro(pentamethylcyclopentadienyl)rhodium (III) (1R,2R)-N-(p-toluenesulfonyl)-1,2-diphenylethylenediamine (0.67 mg, 0.001 mmol, s/c=500) in ethyl acetate (0.5 ml), followed by stirring at room temperature for 2 hours. After completion of the reaction, the reaction mixture was purified by silica gel column chromatography to give a desired compound, (2R, 3S)-3-(p-toluenesulfonyl)amino-1-chloro-2-hydroxy-4-phenylbutane (173.5 mg; yield: 98.3%). HPLC analysis revealed that the production ratio of the desired (2R,3S)-form to the isomeric (2S,3S)-form, (2R,3S):(2S,3S), was 10.9:1. The results of elementary analysis were as follows.

Calcd. C, 57.70%; H, 5.70%; N, 3.96%. Found C, 57.57%; H, 5.51%; N, 3.64%.

Example 30

In the same manner as in Example 29, except for using a solution of chloro(pentamethylcyclopentadienyl)rhodium (III) (1S,2S)-N-(p-toluenesulfonyl)-1,2-diphenylethylenediamine (0.34 mg, 0.005 mmol, s/c=1000) in ethyl acetate (0.5 ml), a desired compound (2S,3S)-3-(p-toluenesulfonyl)amino-1-chloro-2-hydroxy-4- phenylbutane (170.3 mg; yield: 96.3%) was obtained. HPLC analysis revealed that the production ratio of the desired (2S,3S)-form to the isomeric (2R,3S)-form, (2S,3S):(2R,3S), was 44.8:1. The results of elementary analysis were as follows.

Calcd. C, 57.70%; H, 5.70%; N, 3.96%. Found C, 57.70%; H, 5.50%; N, 3.79%.

Example 31

(3S)-3-Benzyloxycarbonylamino-1-chloro-5-methyl-2-hexanone (298.7 mg, 1.0 mmol) and a formic acid/triethylamine azeotropic mixture (0.2 ml) were added to a solution of chloro(pentamethylcyclopentadienyl)rhodium (III) (1R,2R)-N-(p-toluenesulfonyl)-1,2-diphenylethylenediamine (0.67 mg, 0.001 mmol, s/c=1000) in ethyl acetate (1.0 ml), followed by stirring at room temperature for 2 hours. After completion of the reaction, the reaction mixture was purified by silica gel column chromatography to give a desired compound, (2R, 3S)-3-benzyloxycarbonylamino-1-chloro-2-hydroxy-5-methylhexane (295.6 mg; yield: 98.5%). HPLC analysis revealed that the production ratio of the desired (2R,3S)-form to the isomeric (2S,3S)-form, (2R,3S):(2S,3S), was 4.9:1. The results of elementary analysis were as follows.

Calcd. C, 60.10%; H, 7.40%; N, 4.67%. Found C, 59.87%; H, 7.39%; N, 4.47%.

Example 32

In the same manner as in Example 31, except for using a solution of chloro(pentamethylcyclopentadienyl)rhodium (III) (1S,2S)-N-(p-toluenesulfonyl)-1,2-diphenylethylenediamine (0.67 mg, 0.001 mmol, s/c=1000) in ethyl acetate (1.0 ml), a desired compound (2S,3S)-3-benzyloxycarbonylamino-1-chloro-2-hydroxy-5-methylhexane (260.6 mg; yield: 86.7%) was obtained. HPLC analysis revealed that the production ratio of the desired (2S,3S)-form to the isomeric (2R,3S)-form, (2S,3S):(2R,3S), was 7.7:1. The results of elementary analysis were as follows.

Calcd. C, 60.10%; H, 7.40%; N, 4.67%. Found C, 60.23%; H, 7.41%; N, 4.58%.

Example 33

(3S)-3-Benzoylamino-1-chloro-4-phenyl-2-butanone (301.8 mg, 1.0 mmol) and a formic acid/triethylamine azeotropic mixture (0.2 ml) were added to a solution of chloro(pentamethylcyclopentadienyl)rhodium (III) (1R, 2R)-N-(p-toluenesulfonyl)-1,2-diphenylethylenediamine (0.67 mg, 0.001 mmol, s/c=1000) in ethyl acetate (0.5 ml), followed by stirring at room temperature for 2 hours. After completion of the reaction, the reaction mixture was purified by silica gel column chromatography to afford a desired compound, (2R, 3S)-3-benzoylamino-1-chloro-2-hydroxy- 4-phenylbutane (300.1 mg; yield: 98.8%). The production ratio of the desired (2R,3S)-form to the isomeric (2S,3S)-form, (2R,3S):(2S,3S), was 27.3:1. The results of elementary analysis were as follows.

Calcd. C, 67.21%; H, 5.97%; N, 4.61%. Found C, 66.96%; H, 5.89%; N, 4.61%.

Example 34

(3S)-3-Benzoylamino-1-chloro-4-phenyl-2-butanone (301.8 mg, 1.0 mmol) and a formic acid/triethylamine azeotropic mixture (0.2 ml) were added to a solution of chloro(pentamethylcyclopentadienyl)rhodium (III) (1S,2S)-N-(p-toluenesulfonyl)-1,2-diphenylethylenediamine (0.67 mg, 0.001 mmol, s/c=1000) in ethyl acetate (0.5 ml), followed by stirring at room temperature for 2 hours. Quantitative analysis by HPLC revealed production of a desired compound, (2S, 3S)-3-benzoylamino-1-chloro-2-hydroxy-4-phenylbutane (295.6 mg; yield: 97.3%). The production ratio of the desired (2S,3S)-form to the isomeric (2R,3S)-form, (2S,3S):(2R,3S), was 22.6:1. The results of elementary analysis were as follows.

Calcd. C, 67.21%; H, 5.97%; N, 4.61%. Found C, 67.22%; H, 5.84%; N, 4.50%.

Example 35

(3S)-3-Benzyloxycarbonylamino-1-chloro-4-naphthyl-2-butanone (190.9 mg, 0.5 mmol) and a formic acid/triethylamine azeotropic mixture (0.1 ml) were added to a solution of chloro(pentamethylcyclopentadienyl)rhodium (III) (1R,2R)-N-(p-toluenesulfonyl)-1,2-diphenylethylenediamine (0.34 mg, 0.0005 mmol, s/c=1000) in ethyl acetate (1.01ml), followed by stirring at room temperature for 2 hours. After completion of the reaction, purification by silica gel column chromatography afforded a desired compound, (2R,3S)-3-benzyloxycarbonylamino-1-chloro-2-hydroxy-4-naphthylbutane (190.1 mg; yield: 99.1%). As a result of HPLC analysis, the production ratio of the desired (2R,3S)-form to the isomeric (2S,3S)-form, (2R,3S):(2S,3S), was 9.5:1. The results of elementary analysis were as follows.

Calcd. C, 68.84%; H, 5.78%; N, 3.65%. Found C, 68.68%; H, 5.65%; N, 3.55%.

Example 36

(3S)-3-Benzyloxycarbonylamino-1-chloro-4-naphthyl-2-butanone (190.1 mg, 0.5 mmol) and a formic acid/triethylamnine azeotropic mixture (0.1 ml) were added to a solution of chloro(pentamethylcyclopentadienyl)rhodium (III) (1S,2S)-N-(p-toluenesulfonyl)-1,2-diphenylethylenediamine (0.34 mg, 0.0005 mmol, s/c=1000) in ethyl acetate (0.5 ml), followed by stirring at room temperature for 2 hours. After completion of the reaction, purification by silica gel column chromatography gave a desired compound, (2S,3S)-3-benzyloxycarbonylamino-1-chloro-2-hydroxy-4-naphthylbutane (179.0 mg; yield: 93.3%). As a result of HPLC analysis, the production ratio of the desired (2S,3S)-form to the isomeric (2R,3S)-form, (2S,3S):(2R,3S), was 10.9:1. The results of elementary analysis were as follows.

Calcd. C, 68.84%; H, 5.78%; N, 3.65%. Found C, 68.99%; H, 5.68%; N, 3.57%.

Example 37

(3S)-3-Benzyloxycarbonylamino-1-chloro4-(p-fluorophenyl)-2-butanone (174.9 mg, 0.5 mmol) and a formic acid/triethylamine azeotropic mixture (0.1 ml) were added to a solution of chloro(pentamethylcyclopentadienyl) rhodium (III) (1R,2R)-N-(p-toluenesulfonyl)-1,2-diphenylethylenediamine (0.34 mg, 0.0005 mmol, s/c=1000) in ethyl acetate (1.0 ml), followed by stirring at room temperature for 2 hours. After completion of the reaction, the reaction mixture was purified by silica gel column chromatography to give a desired compound, (2R,3S)-3-benzyloxycarbonylamino-1-chloro-2-hydroxy-4-(p-fluorophenyl)butane (166.2 mg; yield: 94.4%). As a result of HPLC analysis, the production ratio of the desired (2R,3S)-form to the isomeric (2S,3S)-form, (2R,3S):(2S,3S), was 6.7:1. The results of elementary analysis were as follows.

Calcd. C, 61.45%; H, 5.44%; N, 3.98%. Found C, 61.52%; H, 5.22%; N, 3.90.

Example 38

(3S)-3-Benzyloxycarbonylamino-1-chloro-4-(p-fluorophenyl)-2-butanone (174.9 mg, 0.5 mmol) and a formic acid/triethylamine azeotropic mixture (0.1 ml) were added to a solution of chloro(pentamethylcyclopentadienyl) rhodium (III) (1S,2S)-N-(p-toluenesulfonyl)-1,2-diphenylethylenediamine (0.34 mg, 0.0005 mmol, s/c=1000) in ethyl acetate (1.0 ml), followed by stirring at room temperature for 2 hours. After completion of the reaction, the reaction mixture was purified by silica gel column chromatography to give a desired compound, (2S,3S)-3-benzyloxycarbonylamino-1-chloro-2-hydroxy-4-(p-fluorophenyl)butane (160.1 mg; yield: 91.0%). As a result of HPLC analysis, the production ratio of the desired (2S,3S)-form to the isomeric (2R,3S)-form, (2S,3S):(2R,3S), was 18.3:1. The results of elementary analysis were as follows.

Calcd. C, 61.45%; H, 5.44%; N, 3.98%. Found C, 61.65%; H, 5.29%; N, 3.88%.

Example 39

(3S-3-tert-Butoxycarbonylamino-1-chloro-5-methyl-2-hexanone (263.8 mg, 1.0 mmol) and a formic acid/triethylamine azeotropic mixture (0.2 ml) were added to a solution of chloro(pentamethylcyclopentadienyl)rhodium (III) (1R,2R)-N-(p-toluenesulfonyl)-1,2-diphenylethylenediamine (0.67 mg, 0.0001 mmol, s/c=1000) in ethyl acetate (1.0 ml), followed by stirring at room temperature for 2 hours. After completion of the reaction, the reaction mixture was purified by silica gel column chromatography to give a desired compound, (2R,3S)-3-tert-butoxycarbonylamino-1-chloro-2-hydroxy-4-methylhexane (250.0mg; yield: 94.1%). As a result of HPLC analysis, the production ratio of the desired (2R,3S)-form to the isomeric (2S,3S)-form, (2R,3S):(2S,3S), was 4.9:1. The results of elementary analysis were as follows.

Calcd. C, 54.23%: H, 9.10%; N, 5.27%. Found C, 54.47%; H, 9.14%; N, 5.17%.

Example 40

(3S)-3-tert-Butoxycarbonylamino-1-chloro-5-methyl-2-hexanone (263.8 mg, 1.0 mmol) and a formic acid/triethylamine azeotropic mixture (0.2 ml) were added to a solution of chloro(pentamethylcyclopentadienyl)rhodium (III) (1S,2S)-N-(p-toluenesulfonyl)-1,2-diphenylethylenediamine (0.67 mg, 0.0001 mmol, s/c=1000) in ethyl acetate (1.0 ml), followed by stirring at room temperature for 2 hours. After completion of the reaction, the reaction mixture was purified by silica gel column chromatography to give a desired compound, (2S,3S)-3-tertbutoxycarbonylamino-1-chloro-2-hydroxy-5-methylhexane (255.8 mg; yield: 96.4%). As a result of HPLC analysis, the production ratio of the desired (2S,3S)-form to the isomeric (2R,3S)-form, (2S,3S):(2R,3S), was 7.7:1. The results of elementary analysis were as follows.

Calcd. C, 54.23%: H, 9.10%; N, 5.27%. Found C, 54.35%; H, 9.21%; N, 5.15%.

Example 41

2-Chloro-3'-chloroacetophenone (94.5 mg; 0.5 mmol) and a formic acid/triethylamine azeotropic mixture (0.1 ml) were added to a solution of chloro(pentamrethylcyclopentadienyl)iridium (III) (1R,2R)-N-(p-toluenesulfonyl)-1,2-diaminocyclohexane (3.5 mg, 0.0005 mmol, s/c=100) in ethyl acetate (0.5 ml), followed by stirring at room temperature for 16 hours. After completion of the reaction, the reaction mixture was purified by silica gel column chromatography to give a desired compound, (+)-2-chloro-1-(3'-chlorophenyl)ethanol (88.5 mg; yield: 92.7%; optical purity: 91.0%).

Reference Example 1

A solution of tetrachlorobis(p-cymene)diruthenium (II) (3.1 mg, 0.005 mmol) and (1R,2R)-N-(p-toluenesulfonyl)-1,2-diphenylethylenediamine (7.3 mg, 0.02 mmol) in isopropyl alcohol (5.0 ml) was heated at 80° C. for 20 minutes while stirring. After cooling the solution to room temperature, a 0.1 potassium tert-butoxide isopropyl alcohol solution (0.5 ml, 0.05 mmol) and a solution of 2-chloroacetophenone (154.6 mg, 1.0 mmol) in isopropyl alcohol (4.5 ml) were added thereto, followed by stirring at room temperature for 14 hours. After completion of the reaction, the solvent was removed by evaporation, and the residue was purified by silica gel column chromatography to recover the starting 2-chloroacetophenone (148.0mg; recovery: 96.0%).

Reference Example 2

The same reaction as in Reference Example 1 was carried out, except for replacing (1R,2R)-N(p-toluenesulfonyl)-1,2-diphenylethylenediamine used as an optically active bidentate ligand with (1S,2R)-cis-1-amino-2-indanol (3.0 mg, 0.02 mmol), to recover the starting 2-chloroacetophenone (147.0 mg; recovery: 95.0%).

Reference Example 3

The same reaction as in Reference Example 1 was carried out, except for replacing tetrachlorobis(p-cymene)diruthenium (II) used as a metal complex with di-μ-chlorodichlorobis(pentamethylcyclopentadienyl)dirhodium (III) (3.1 mg, 0.005 mmol) and replacing (1R,2R)-N-(p-toluenesulfonyl)-1,2-diphenylethylenediamine used as an optically active bidentate ligand with (1S,2R)-cis-1-amino-2-indanol (3.0 mg, 0.02 mmol), to recover the starting 2-chloroacetophenone (141.0 mg; recovery: 91.0%).

Reference Example 4

The same reaction as in Reference Example 1 was carried out, except for replacing tetrachlorobis(p-cymene)diruthenium (II) used as a metal complex with di-μ-chlorodichlorobis(pentamethylcyclopentadienyl)dirhodium (III) (3.1 mg, 0.005 mmol) and replacing (1R,2R)-N-(p-toluenesulfonyl)-1,2-diphenylethylenediamine used as an optically active bidentate ligand with (1R,2R)-N-(p-toluenesulfonyl)-1,2-cyclohexanediamine (5.4 mg, 0.02 mmol), to obtain a desired compound, (+)-2-chloro-1-phenylethanol (46.8 mg; yield: 29.9%; optical purity: 96.1% ee).

Reference Example 5

2-Chloro-3'-chloroacetophenone (189.6 mg; 1.0 mmol) and a formic acid/triethylamine azeotropic mixture (0.1 ml) were added to a solution of chloro(cymene)ruthenium (II) (1R,2R)-N-(p-toluenesulfonyl)-1,2-diphenylethylenediamine (1.3 mg, 0.002 mmol, s/c=500) in ethyl acetate (1.0 ml), followed by stirring at room temperature for 2 hours. It was confirmed by NMR that the conversion to a desired compound, (+)-2-chloro-1-(3'-chlorophenyl)ethanol, was 14.1%; the conversion to a by-product, 2-formyloxy-3'-chloroacetophenone, was 9.5%; and 76.7% of the starting compound, 2-chloro-3'-chloroacetophenone, remained unreacted. After 96-hour stirring, the conversion to the desired (+)-2-chloro-1-(3'-chlorophenyl)ethanol was 45.3%; the conversion to the by-produced 2-formyloxy-3'-chloroacetophenone was 25.9%; and 28.7% of the starting 2-chloro-3'-chloroacetophenone remained unreacted. The enantiomer excess of the (+)-2-chloro-1-(3'-chlorophenyl)ethanol was 88.2%.

INDUSTRIAL APPLICABILITY

According to the present invention, an optically active halohydrin compound can be prepared from an α-haloketone compound in high yield and high optical yield.

What is claimed is:

1. A process of preparing an optically active halohydrin compound represented by general formula (3), comprising reducing an α-haloketone compound represented by general formula (1) by asymmetric hydrogen transfer in the presence of a group 9 transition metal compound having a substituted or unsubstituted cyclopentadienyl group and an optically active diamine compound represented by general formula (2);

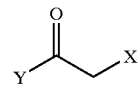
(1)

wherein X represents a halogen atom; Y represents an aromatic hydrocarbon group, an aromatic heterocyclic group, an unsaturated hydrocarbon group or

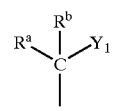

wherein $R^a$ and $R^b$ each represent a hydrogen atom, a substituted or unsubstituted alkyl group having 1 to 10 carbon atoms, a substituted or unsubstituted aryl group having 6 to 15 carbon atoms or a substituted or unsubstituted aralkyl group having 7 to 20 carbon atoms, in which the alkyl, aryl and aralkyl group may contain a hetero atom in the carbon skeleton thereof; and $Y_1$ represents an amino group, a protected amino group, a hydroxyl group or a protected hydroxyl group;

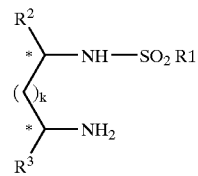

(2)

wherein $R^1$ represents an alkyl group, a fluoroalkyl group or a substituted or unsubstituted phenyl group; $R^2$ and $R^3$, which may be the same or different, each represent a substituted or unsubstituted phenyl group or a substituted or unsubstituted alkyl group having 1 to 10 carbon atoms, or $R^2$ and $R^3$ are taken together to form a ring; * indicates an asymmetric carbon; k represents an integer of 0 to 3; and the steric configuration is (S,S) or (R,R);

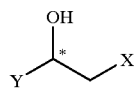

(3)

wherein X and Y are as defined above, and * indicates an asymmetric carbon.

2. The process of preparing an optically active halohydrin compound according to claim 1, wherein the asymmetric hydrogen transfer reduction is carried out in the presence of a base.

3. The process of preparing an optically active halohydrin compound according to claim 1, wherein the optically active diamine compound represented by general formula (2) is the one in which $R^1$ is a p-methylphenyl group, and $R^2$ and $R^3$ are each a phenyl group.

4. The process of preparing an optically active halohydrin compound according to claim 1, wherein the group 9 transition metal compound having a substituted or unsubstituted cyclopentadienyl group is di-$\mu$-chlorodichlorobis(pentamethylcyclopentadienyl)dirhodium (III).

5. The process of preparing an optically active halohydrin compound according to claim 1, wherein the group 9 transition metal compound having a substituted or unsubstituted cyclopentadienyl group and the optically active diamine compound represented by general formula (2) are allowed to react in a solvent, and the α-haloketone compound represented by general formula (1) is added to the resulting reaction mixture.

6. The process of preparing an optically active halohydrin compound according to claim 1, wherein the group 9 transition metal compound having a substituted or unsubstituted cyclopentadienyl group and the optically active diamine compound represented by general formula (2) are allowed to react in a solvent, a chiral metal complex represented by general formula (23) is collected from the resulting reaction mixture by filtration, and the α-haloketone compound represented by general formula (1) is asymmetrically reduced by using the collected chiral metal complex as an asymmetric catalyst;

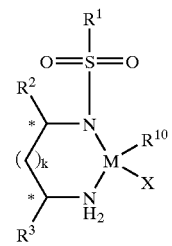

(23)

wherein $R^1$, $R^2$, $R^3$, k, and X are as defined above; $R^{10}$ represents a substituted or unsubstituted cyclopentadienyl group; M represents a group 9 transition metal; * indicates an asymmetric carbon; and the steric configuration of the optically active amine compound moiety is (R,R) or (S,S).

7. The process of preparing an optically active halohydrin compound according to claim 1, wherein the asymmetric reduction is carried out in the presence of a hydrogen-donating organic compound or a hydrogen-donating inorganic compound.

8. The process of claim 1, further comprising contacting the optically active halohydrin compound with a base to form an epoxide of formula (4);

(4)

wherein Y is as defined in general formula (1); and * indicates an asymmetric carbon.

9. The process of preparing an optically active halohydrin compound according to claim 1, wherein the optically active diamine compound represented by general formula (2) is an optically active diphenylethylenediamine compound represented by general formula (20);

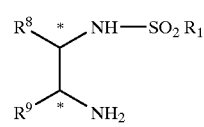

(20)

wherein $R^1$ is as defined above; $R^8$ and $R^9$, which may be the same or different, each represent a substituted or unsubstituted phenyl group; * indicates an asymmetric carbon; and the steric configuration is (1S,2S) or (1R, 2R).

10. The process of preparing an optically active halohydrin compound according to claim 9, wherein the asymmetric hydrogen transfer reduction is carried out in the presence of a base.

11. The process of preparing an optically active halohydrin compound according to claim 9, wherein the opticallyactive diphenylethylenediamine compound represented by general formula (20) is the one in which $R^1$ is a p-methylphenyl group, and $R^8$ and $R^9$ are each a phenyl group.

12. The process of preparing an optically active halohydrin compound according to claim 9, wherein the group 9 transition metal compound having a substituted or unsubstituted cyclopentadienyl group is di-$\mu$-chlorodichlorobis(pentamethylcyclopentadienyl)dirhodium (III).

13. The process of preparing an optically active halohydrin compound according to claim 9, wherein the group 9 transition metal compound having a substituted or unsubstituted cyclopentadienyl group and the optically active diphenylethylenediamine compound represented by general formula (20) are allowed to react in a solvent, and the α-haloketone compound represented by general formula (1) is added to the resulting reaction mixture.

14. The process of preparing an optically active halohydrin compound according to claim 9, wherein the group 9 transition metal compound having a substituted or unsubstituted cyclopentadienyl group and the optically active diphenylethylenediamine compound represented by general formula (20) are allowed to react in a solvent, a chiral metal complex represented by general formula (24) is collected from the resulting reaction mixture by filtration, and the α-haloketone compound represented by general formula (1) is asymmetrically reduced by using the-collected chiral metal complex as an asymmetric catalyst;

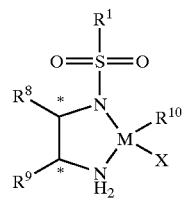

(24)

wherein $R^1$, $R^8$, $R^9$, $R^{10}$, M, and X are as defined above; * indicates asymmetric carbon; and the steric configuration of the optically active diphenylethylenediamine compound moiety is (1R,2R) or (1S,2S).

15. The process of preparing an optically active halohydrin compound according to claim 9, wherein the asymmetric reduction is carried out in the presence of a hydrogen-donating organic compound or a hydrogen-donating inorganic compound.

16. The process of claim 9, further comprising contacting the optically active halohydrin compound with a base to form an epoxide of formula (4);

(4)

wherein Y is as defined in general formula (1); and * indicates an asymmetric carbon.

* * * * *

UNITED STATES PATENT AND TRADEMARK OFFICE
CERTIFICATE OF CORRECTION

PATENT NO. : 6,888,012 B2
DATED : May 3, 2005
INVENTOR(S) : Takayoshi Torii et al.

It is certified that error appears in the above-identified patent and that said Letters Patent is hereby corrected as shown below:

<u>Column 5,</u>
Line 9, "or a substituent" should read -- or a substituent. --;
Line 39, "N,N-benzylamino," should read -- N,N-dibenzylamino, --.

<u>Column 12,</u>
Line 59, "(155 mg," should read -- (15.5 mg, --.

<u>Column 13,</u>
Line 51, "replacing 2chloro-3'-" should read -- replacing 2-chloro-3'- --.

<u>Column 14,</u>
Line 36, "4benzo[1,3]dioxo-5yl-1-chloro-3-buten-2-one" should read
-- 4-benzo[1,3]dioxo-5yl-1-chloro-3-buten-2-one --.

Signed and Sealed this

Sixteenth Day of August, 2005

JON W. DUDAS
*Director of the United States Patent and Trademark Office*